United States Patent
Teder (10) Patent No.: US 8,271,198 B2
(45) Date of Patent: Sep. 18, 2012

(54) OPTICAL MOISTURE SENSOR

(75) Inventor: Rein S. Teder, Bloomington, MN (US)

(73) Assignee: Hydreon Corporation, Eden Prairie, MN (US)

( * ) Notice: Subject to any disclaimer, the term of this patent is extended or adjusted under 35 U.S.C. 154(b) by 252 days.

(21) Appl. No.: 12/850,750

(22) Filed: Aug. 5, 2010

(65) Prior Publication Data

US 2011/0054794 A1    Mar. 3, 2011

Related U.S. Application Data

(60) Provisional application No. 61/237,715, filed on Aug. 28, 2009.

(51) Int. Cl.
*G06F 1/14* (2006.01)
(52) U.S. Cl. .......................................................... 702/3
(58) Field of Classification Search ........................ 702/3
See application file for complete search history.

(56) References Cited

U.S. PATENT DOCUMENTS

| | | |
|---|---|---|
| 3,705,533 A | 12/1972 | Kahl |
| 3,808,385 A | 4/1974 | Klinefelter |
| 4,355,271 A | 10/1982 | Noack |
| 5,059,877 A | 10/1991 | Teder |
| 5,796,106 A | 8/1998 | Noack |

(Continued)

FOREIGN PATENT DOCUMENTS

DE    10209349 C1    5/2003

(Continued)

OTHER PUBLICATIONS

Monitoring the Curing Process of Concrete Composites Using Plastic Optic Fiber Sensors, 16th International Conference on composite materials, 2007, p. 1-7.*

*Primary Examiner* — Tung S Lau (57) ABSTRACT

A moisture sensor is provided that simultaneously achieves ruggedness, sensitivity, wide dynamic range, versatility of application, and low cost. The outer, top service of the sensor is a lens having a predetermined geometric shape which preferably makes the rain sensor resistant to the build up of debris on the outer surface as well as being effectively self-cleaning. Within a housing of the rain sensor, at least one light emitter and at least one light detector are each deployed on a substantially planar circuit board facing such outer lens surface. So arranged, light rays from the at least one emitter strike the outer lens surface and is reflected about 90°, whereupon it strikes the outer lens surface once more and is again reflected therefrom about 90° to focus back onto the at least one detector. Raindrops present on the outside surface of the sensor affect the intensity of the light rays reflected and signals from the at least one light detector are sent to control circuitry within the rain sensor. A microprocessor in the sensor processes the resulting data to detect rain intensity over a wide range so as to be capable of being effectively deployed for applications such as to emulate a tipping bucket style rain detector, providing condensation sensing, and automatically adjusting the strength of the light rays emitted by the at least one light emitter to provide improved consistency of operation of the sensor over time.

20 Claims, 4 Drawing Sheets

U.S. PATENT DOCUMENTS

| | | |
|---|---|---|
| 5,836,339 A | 11/1998 | Klever |
| 5,852,284 A | 12/1998 | Teder |
| 5,898,183 A | 4/1999 | Teder |
| 5,946,084 A | 8/1999 | Kubulins |
| 6,091,065 A | 7/2000 | Teder |
| 6,144,017 A | 11/2000 | Millett |
| 6,582,658 B1 * | 6/2003 | Hood et al. .................. 422/401 |
| 2004/0129884 A1 | 7/2004 | Boyle |

FOREIGN PATENT DOCUMENTS

| | | |
|---|---|---|
| DE | 102005016640 A1 | 10/2006 |
| FR | 2694629 A1 | 2/1994 |
| JP | 62028642 A | 2/1987 |
| WO | WO 02/098716 A1 | 12/2002 |

* cited by examiner

OPTICAL MOISTURE SENSOR

RELATED APPLICATION

This application is claiming the benefit, under 35 U.S.C. 119(e), of the provisional application filed Aug. 28, 2009 under 35 U.S.C. 111(b), which was granted Ser. No. 61/237,715. This provisional application is hereby incorporated by reference in its entirety.

BACKGROUND

The present invention relates to an optical moisture sensor. More particularly, the present invention relates to a self-contained optical moisture sensor suitable for a wide variety of non-vehicular applications.

Rain sensors for use in vehicular applications are well known. Rain and moisture sensors for various non-vehicular applications are also known in the patent literature, for example:

U.S. Pat. No. 3,705,533 describes a precipitation sensor having two buckets secured to each other for tilting movement between two end positions, is provided with a precipitation collecting and distributing means which collects precipitation during tilting of the buckets and has a normally closed valve operated by the buckets to open when the same are in the end positions so that the collected precipitation is alternately discharged into the buckets. Evaporation retarding covers with small inlet cutouts close the tops of the buckets without bouncing back, and magnetic switch means generate a counting pulse for each tilting movement.

U.S. Pat. No. 3,808,385 describes a moisture responsive actuator for controlling the operation of a fluid operated sprinkling system, irrigation system or the like. The moisture responsive actuator is provided with hygoscopic material which expands in response to contact with rain water to depress a switch to deactivate the sprinkling system, the hygroscopic material contracting upon drying to release the switch, whereupon the sprinkling system is activated.

U.S. Pat. No. 5,796,106 describes a detector for detecting the presence of ice, water, mist, frost or other solids or liquids on a sensing surface. The sensing surface is a medium substantially transparent to electromagnetic radiation and solids or liquids are deposited on such sensing surface. A transmitter directs radiation onto the sensing surface and a receiver is responsive to radiation reflected from the surface. A discriminator circuit receives an output from the receiver and provides an output indicative of whether a solid or liquid is present on the surface.

U.S. Pat. No. 5,836,339 describes a raindrop counter and control system for irrigation systems which is said to provide for quick detection of the presence and subsequent absence of precipitation once it has first been detected. The counter and control system disables normal operation of, for example, automatic irrigation systems by interrupting power to the irrigation valves during and after detection of precipitation. Various features including sensitivity selections and varied delay periods are also described. The apparatus includes a small outdoor probe, and a separate control and display unit for interacting with a plurality of automated systems.

Notwithstanding the efforts noted above, moisture sensing in a number of non-vehicular applications could clearly benefit from an improved moisture sensor. For example, self-closing skylights and windows exist, but are relatively rare because of the lack of sufficiently sensitive moisture sensors. Condensation sensing in heating, cooling and ventilation systems is rarely done, because no currently available sensor is sufficiently reliable. Remote meteorological stations are in use, but require maintenance for the tipping bucket rain gauge. Accurate recording of moisture in desert environments does not occur because available sensor systems are not sufficiently sensitive.

Accordingly, what is needed is an optical moisture sensor which is versatile, rugged, provides a sizeable sensed area so as to be sensitive to extremes, high and low, of humidity and precipitation events, is low maintenance, and low in cost.

SUMMARY OF THE INVENTION

The present invention relates to a self-contained optical moisture sensor unit comprising a housing or base member, a circuit board disposed substantially horizontally within the housing, at least one light emitter, and at least one light detector being mounted on the circuit board, a lens sealingly mounted to the housing, the lens being of a predetermined geometric shape. The lens has an inner sensing surface and an outer sensing surface. The outer sensing surface of the lens is, preferably, generally concave relative to the substantially horizontal circuit board and is also preferably substantially symmetrical with respect to the circuit board. The inner sensing surface of the lens is preferably a compound shape, comprising a central substantially concave portion and peripheral substantially planar portions proximate and above each of the at least one light emitter and at least one light detector.

The lens is capable of receiving and transmitting therethrough, solar radiation on the outer sensing surface from sources external to the self-contained moisture sensor unit, as well as reflecting light rays from the inner sensing surface emitted by the at least one light emitter disposed within the self-contained moisture sensor unit.

The moisture sensor of the present invention has a center axis which is between 68% and 80%, of the radius of the outer sensing surface of the lens.

The moisture sensor of the present invention also comprises control circuitry to control the at least one light emitter, provides other desirable functions, features in hardware and software which allow the moisture sensor to be configured for different applications.

DETAILED DESCRIPTION OF THE INVENTION

The present invention relates to a self-contained optical moisture sensor suitable for a wide variety of non-vehicular applications.

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

While automotive optical rain sensors are well adapted for the purpose of, for example, windshield wiper control, they generally must be rigidly affixed to glass or some other substrate material and housed in a watertight container. Thus, they are not directly suited for non-vehicular use, such as for use with irrigation systems or meteorological stations. Some reasons why they have not been deployed for non-vehicular use include: the typically flat measurement surface of an automotive rain sensor, if deployed pointing skyward, would be subject to contamination from debris and the like; and if the measurement surface of such a rain sensor was to be deployed at some angle to avoid debris collecting on the surface, it would accurately detect rainfall from only one direction. Additionally, the electrical interfaces typically supplied with automotive rain sensors are intended to solely control windshield wiper and related systems, and are not compatible with non-vehicular systems.

Figure 1:
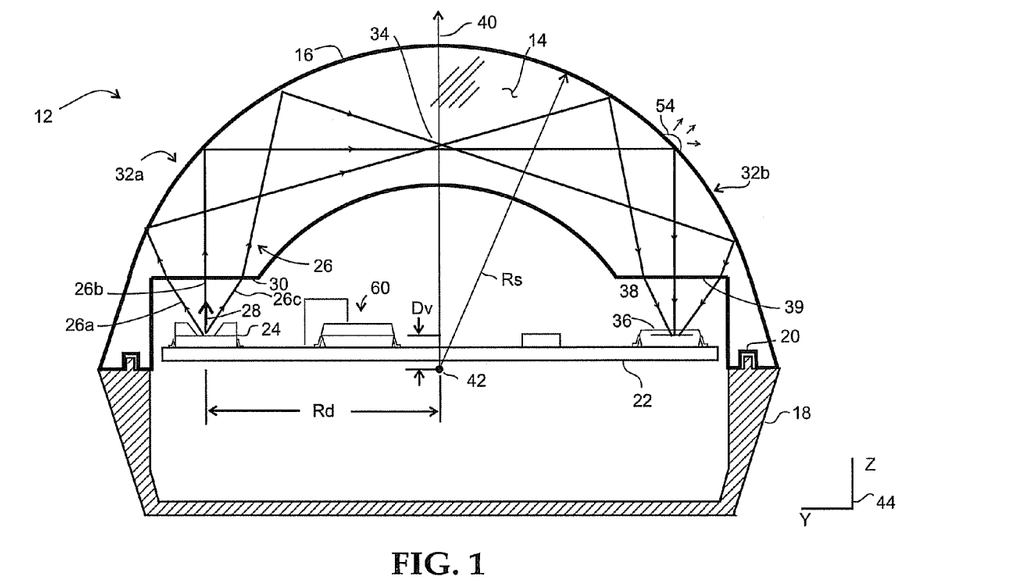
FIG. 1 is a cross-section view of a first embodiment of the moisture sensor according to the present invention, showing the preferred pathway for light rays within the subject moisture sensor in two dimensions.

The moisture sensor 12 is shown in cross-sectional view at FIG. 1. Preferably, a single lens 14 includes all of the optical surfaces needed to realize the moisture sensor of the invention. Lens 14 is preferably molded of a highly light transmissive plastic material such as UV-stabilized polycarbonate or acrylic, but may be made of glass as well. An outer sensing surface 16 is of a predetermined geometric shape, but is preferably generally spherical in shape, presenting an exterior surface that discourages debris and the like from accumulating thereon. In its preferred form, spherical surface 16 is just slightly less than a complete hemisphere, for ease of moldability, and may be considered a hemisphere to a first approximation. The lens 14 is preferably sealingly attached to a housing 18 by a watertight seal 20. Within the enclosed space created by the attached lens 14 and housing 18 of the rain sensor, a planar circuit board 22 having an operational surface 23 is horizontally deployed facing lens 14. At least one light emitter 24 is deployed upon the operational surface 23 of the circuit board 22. The at least one emitter 24 emits a fan of light rays (26a, 26b, 26c) comprising a collimated light beam 26 along an emitter axis 28 normal to the circuit board 22. A planar emitter lens surface 30 is deployed just above the at least one light emitter 24, to gather the rays of light emitted by light emitter 24. Emitter lens surface 30 is a peripheral portion of an inner surface of lens 14. So arranged, planar emitter lens surface 30 reduces the divergence of rays 26a, 26b, 26c from emitter 14. Representative light beam 26 strikes outer lens surface 16 in active emitter sensing region 32a. Also, outer lens surface 16 focuses beam 26, changing it from diverging to converging. A mirror deployed to bend a beam of light 90° is known in the field of optics as a "folding mirror." Folding mirrors are generally planar, however, outer lens surface 16 in the moisture sensor of the present invention acts as a focusing folding mirror in active emitter sensing region 32a.

The now converging beam 26 converges to an approximate focal spot 34, and continues on to become diverging again. The now-diverging horizontal beam 26 strikes outer lens surface 16 a second time at active detector sensing region 32b. In symmetric fashion to the emitter side, the outer lens surface 16 reflects beam 26 downward so as to converge generally toward at least one light detector 36. Just as it did in active emitter sensing area 32a, the outer lens surface acts as a focusing folding mirror in active detector sensing area 32b. At least one light detector 36 is arranged on the same planar circuit board 22 as emitter 24, and has a vertical detection axis 38 generally normal to circuit board 22. A planar, or detector lens 39 is deployed a predetermined distance above light detector 36 causing the converging beam 26 to more strongly converge onto at least one light detector 36.

In a preferred configuration where lens 14 is substantially spherical in shape, a radius (Rs) of the lens 14 has a predetermined geometric relationship to the radial device distance (Rd) from an axis of symmetry 40 of outer surface 16 which can be expressed as $Rd=0.72 \times Rs$. These dimensions may be scaled up or down as needed to make larger or smaller moisture sensors according to the above-mentioned relationship. Preferably, Rd is within a range of from 68 to 80% of Rs. More preferably Rd is 70 to 75% of Rs, most preferably Rd is about 72% of radius Rs. This geometric relationship results in the proper folding and focusing operation to reflect beams 26 from vertical proximate to the emitter to horizontal and back to vertical proximate the at least one detector. The plane of the emitter 24 and detector 36 semiconductor die is preferably located a vertical distance Dv of about 3 mm above a center point 42 of spherical surface 16. FIG. 1 also shows an optical axis direction reference 44 (following the optics convention that Y is out of the page) that will be referred to later in helping to present the optical path in three dimensions. Supports that hold circuit board 22 within housing 18 are not shown for the sake of clarity.

Figures 2, 3:
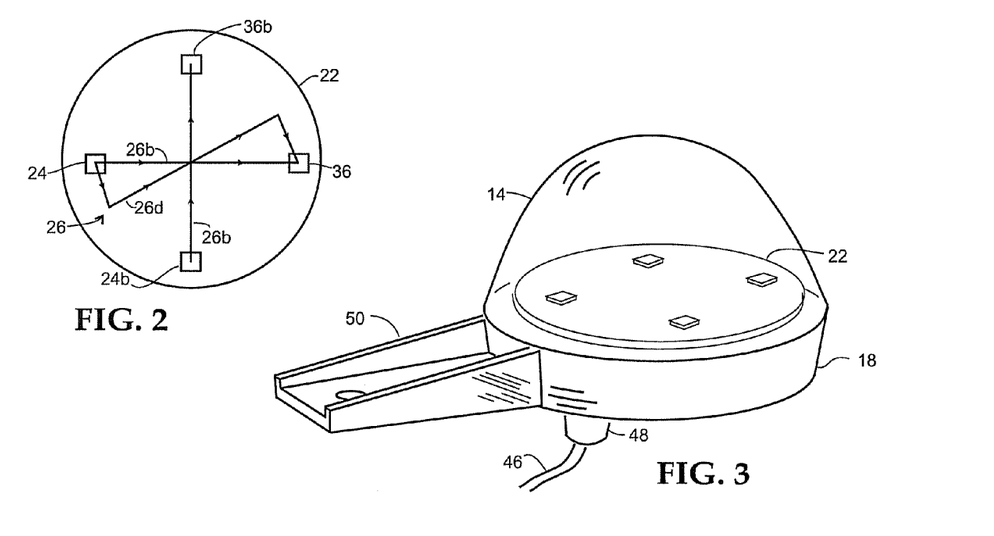
FIG. 2 shows a plan view of the optical path of the first embodiment of the present invention as shown in FIG. 1 where two light emitters and two light detectors are utilized.
FIG. 3 is a perspective view of the rain sensor according to the first embodiment of the present invention as shown in FIGS. 1 and 2.

To provide a greater sensed surface area of the substrate than is available with one light emitter and one light detector, the preferred embodiment of the invention provides a second emitter 24b as well as a second detector 36b at ninety degrees with respect to first emitter 24 and first detector 36 as shown in the top view presented in FIG. 2. FIG. 2 also shows a center ray 26b, and how ray 26d, which is not in the plane of the cross section of FIG. 1 (the y-z plane) is still properly directed from emitters 24 to detectors 36. All of the sensing rays properly reflect off of outside lens surface 16 at an angle of about 90°, even those into and out of the page in FIG. 1. This 90° angle yields optimum sensitivity for an optical moisture sensor. While the addition of the second emitter 24b and second detector 36b yields the best performance, the lowest cost implementation of the sensor may still be utilizing a single emitter 24 and detector 36. Particularly cost sensitive applications, such as automatic closing of residential windows, may use the single emitter/detector configuration.

The moisture sensor of the present invention 12 is shown in perspective view in FIG. 3. Outer lens surface 16 is preferably generally radially symmetric, and housing 18 is thus best implemented as generally complementarily symmetric. Wires 46 to communicate electrical signals to external equipment are brought out through the bottom of housing 18 through a watertight connector 48. A mechanical mounting arm 50 may be provided to mount the sensor where it is needed. In lower cost implementations housing 18 may be molded as an extension of the lens (this is not shown), and the space under the board filled with a potting compound, such as silicone. Because of the hemispherical shape of surface 16, dirt, debris, and falling leaves all will tend to fall harmlessly off of the surface. Water falling on surface 16 will tend to clean away any residue, making the sensing surface effectively "self-cleaning."

Figure 4:
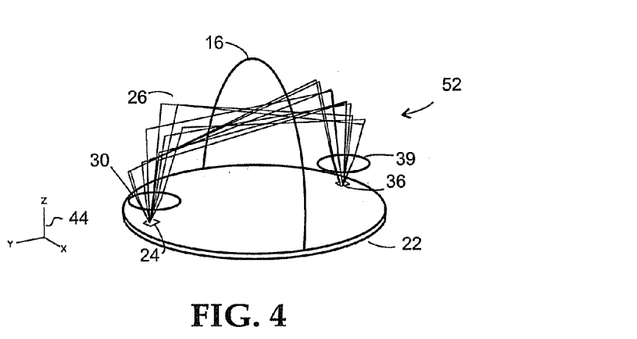
FIG. 4 shows a three-dimensional view illustrating various light rays as directed within the embodiment of FIGS. 1-3 of the moisture sensor according to the present invention.

While the moisture sensor of the invention is most easily understood by examining the optical path in the two-dimensional plane shown in FIG. 1, it should be understood that the device 12 in fact properly directs rays in three-dimensional space. FIG. 4 shows a perspective view of the optical path in three dimensions. Ten of rays 26 selected at random angles from the emitter 24 are depicted. Each of these rays 26 strike outside lens surface 16$n$ three-dimensional space (that is, not necessarily in the plane of FIG. 1), and are properly deflected 90°. It can also be seen that the rays that comprise beam 26 converge to approximate focal point 34 between emitter 24 and detector 36. Axis reference 44, showing its orientation in three dimensions is presented in FIG. 4. The collection of rays comprising beam 26 from emitter 24, through emitter lens 30, reflected off the outside surface 16, through detector lens 39, and to detector 36, comprise the "optical path" 52 of the moisture sensor. The transmission efficiency of optical path 52 is affected when a drop of rain 54 falls on either of the optical sensed regions 32, as shown in FIG. 1.

Figure 5:
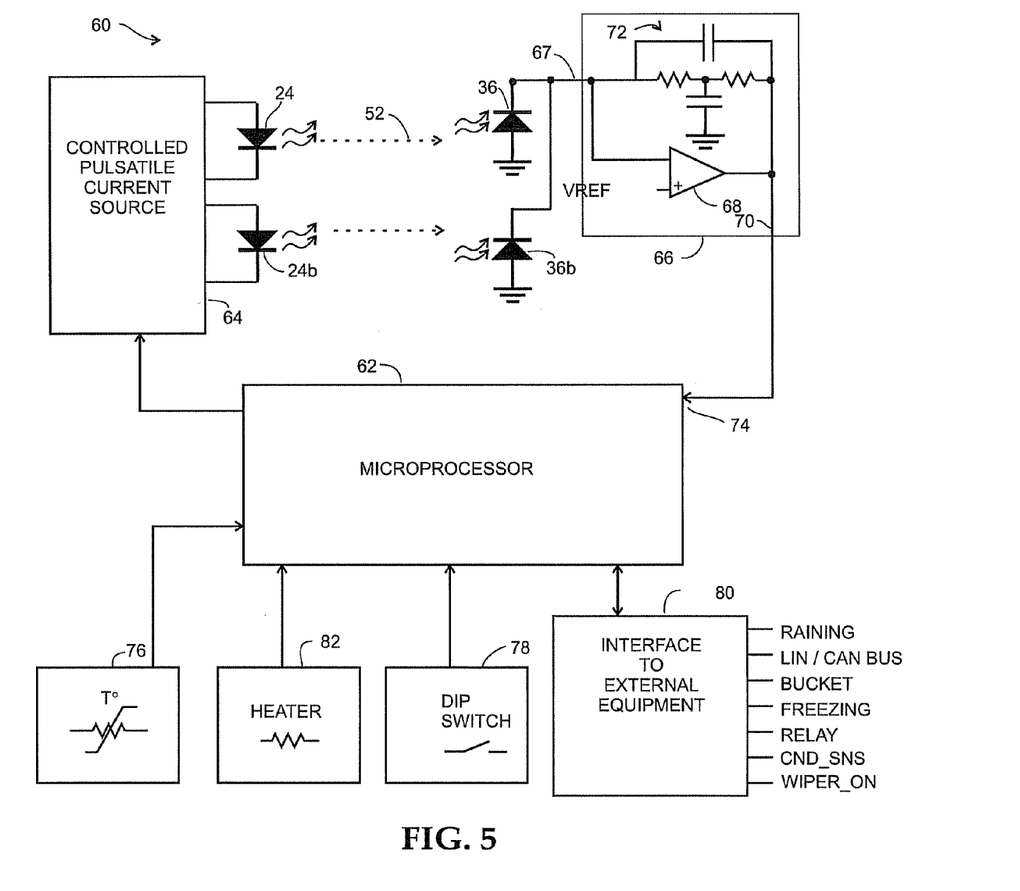
FIG. 5 shows a schematic view of the control circuitry of the moisture sensor according to the present invention as shown in FIG. 1.

Control circuitry 60 is deployed on circuit board 22, and a preferred embodiment of the circuits is presented in a block diagram in FIG. 5. A microprocessor 62 is arranged to generate, receive, and interpret electrical control signals. A controlled current source 64 is operatively connected to microprocessor 62 to produce pulses of current in a preferred embodiment, in emitters 24, 24*b*, causing them to emit pulses of infrared light in alternating fashion. The pulses of light travel through optical path 52, and are received in the preferred embodiment by the detectors 36, 36*b*. The detector is connected to a transimpedance amplifier 66, or current to voltage converter. The active element of transimpedance amplifier 66 is, preferably, an operational amplifier 68. The output 70 of transimpedance amplifier 66 thus produces a series of pulses of amplitude proportional to the signal strength of the light impinging upon the detectors 36, 36*b*. A resistive-capacitive spectral shaping network 72 built into transimpedance amplifier 66 causes the amplifier to have higher gain to ac signals at the frequency of the pulsatile excitation. This spectral shaping helps to reject the influence of dc and low frequency signals, such as sunlight and shadows, as well as higher frequency interference, such as caused by electromagnetic interference (EMI).

Output 70 of transimpedance amplifier 66 is connected to an AC/DC input 74 of microprocessor (alternatively referred to as a computer or processor) 62, which converts the voltage signal into a digital representation. Software within processor 62 is programmed to both generate and respond to the pulsatile excitation. Microprocessor 62 also controls a heater 82, which can be, for example, a simple resistor deployed on circuit board 22, as part of control circuitry 60. Processor 62 also is connected to a thermistor-based temperature sensor 76, so that it may determine the temperature within the housing 18. A multi-pole programming switch (commonly known as a DIP switch) 78 is connected to the processor to configure the moisture sensor of the invention to a chosen application. For example, one particular DIP switch setting may be used to configure the moisture sensor 12 as an emulator for a tipping-bucket type of device, and the output of the device may thus appropriately replicate the pulses produced by a tipping-bucket type of device. Another setting may render the function of the sensor to be an "it's raining" type of sensor (described in greater detail below), and several other DIP switch poles may represent several different adjustment thresholds of an "its raining" configuration of moisture sensor 12.

Interface circuitry 80 allows moisture sensor 12 to communicate or control the application for which the moisture sensor is intended. The interface circuitry includes a power supply, and may include a relay closure, open-collector style output, voltage or current output, serial communications such as RS-232, LIN, or CAN, or a current level shift output. Various outputs are provided depending upon the requirements of the application, such as a freezing indication, a signal to emulate a tipping bucket rain gauge (BUCKET), control wipers (WIPER ON), for non-automotive wiper control applications, condensation sensing (CND_SNS) or a signal to indicate it is raining (RAINING), as will be described later.

In operation, microprocessor 62 controls the current source to produce a pulsatile current signal. Referring to FIG. 1, this causes emitter 24 to emit pulses of infrared light comprising a splay or fan of rays 26*a*, 26*b*, 26*c*, and comprising light beam 26, normal to circuit board 22. Rays 26*a*, 26*b*, 26*c*, strike planar emitter lens surface 30, where each ray is rendered less divergent. Rays 26*a*, 26*b*, 26*c*, continue on to strike outer lens surface 16 in active emitter sensing region 32*a*, where they are reflected or "folded" 90° and rendered convergent. The rays 26*a*, 26*b*, 26*c* strike the surface at about 45° with respect to their points of intersection of the surface, and thus are essentially totally internally reflected (TIR). The rays 26*a*, 26*b*, 26*c* then travel generally parallel to circuit board 22, approximately converging at a focal spot 34, and then diverging again, before striking outer lens surface 16 once more in active detector sensor area 32*b*. Outer lens surface 16 once more folds rays 26*a*, 26*b*, 26*c* 90° towards circuit board 22, and renders rays 26*a*, 26*b*, 26*c* convergent. Rays 26*a*, 26*b*, 26*c* continue toward planar detector lens 29, where they are rendered still more convergent, and focused upon the active sensing surface of light detector 36. Detector 36 is held in a reverse-biased state by transimpedance amplifier 66, causing detector 36 to convert the rays 26*a*, 26*b*, 26*c* to a pulsatile current signal output at an output junction 67 of the photodiode. Operation of the second light emitter 24*b* and second light detector 36*b* is substantially similar to that of light emitter 24 and light detector 36.

In conditions where no moisture is present on outer lens surface 16, optical path 52 is as described above and as depicted in FIGS. 1 and 4. If a water droplet 54 should land or otherwise form upon outside surface 16 of the sensor in active emitter and/or detector sensing regions 32*a*, 32*b*, the refractive index of droplet 54 will approximately match the refractive index of the material of lens 14. This will allow some of rays 26*a*, 26*b*, 26*c* to escape, and thus decrease the intensity of the light reaching detectors 36, 36*b*. The current pulses initiated by light rays 26*a*, 26*b*, 26*c* impinging upon the detectors 36, 36*b* are amplified by transimpedance amplifier 66 and converted to voltage pulses. The amplitude of these voltage pulses are thus affected by the intensity of the light rays 26*a*, 26*b*, 26*c*, which is in turn affected by the presence of water. Raindrops affect the light rays 26*a*, 26*b*, 26*c*, as does any other form of water or liquid that has a refractive index approximately matching that of the sensing surface, here lens material 14. Snow affects the intensity of the light rays if it adheres to the outer lens surface 16. Condensation and frost will similarly affect the intensity of the light rays striking the sensing surface. The moisture sensor 12 of the present invention continues to measure condensation accurately even as relative humidity approaches 100%.

Figure 6:
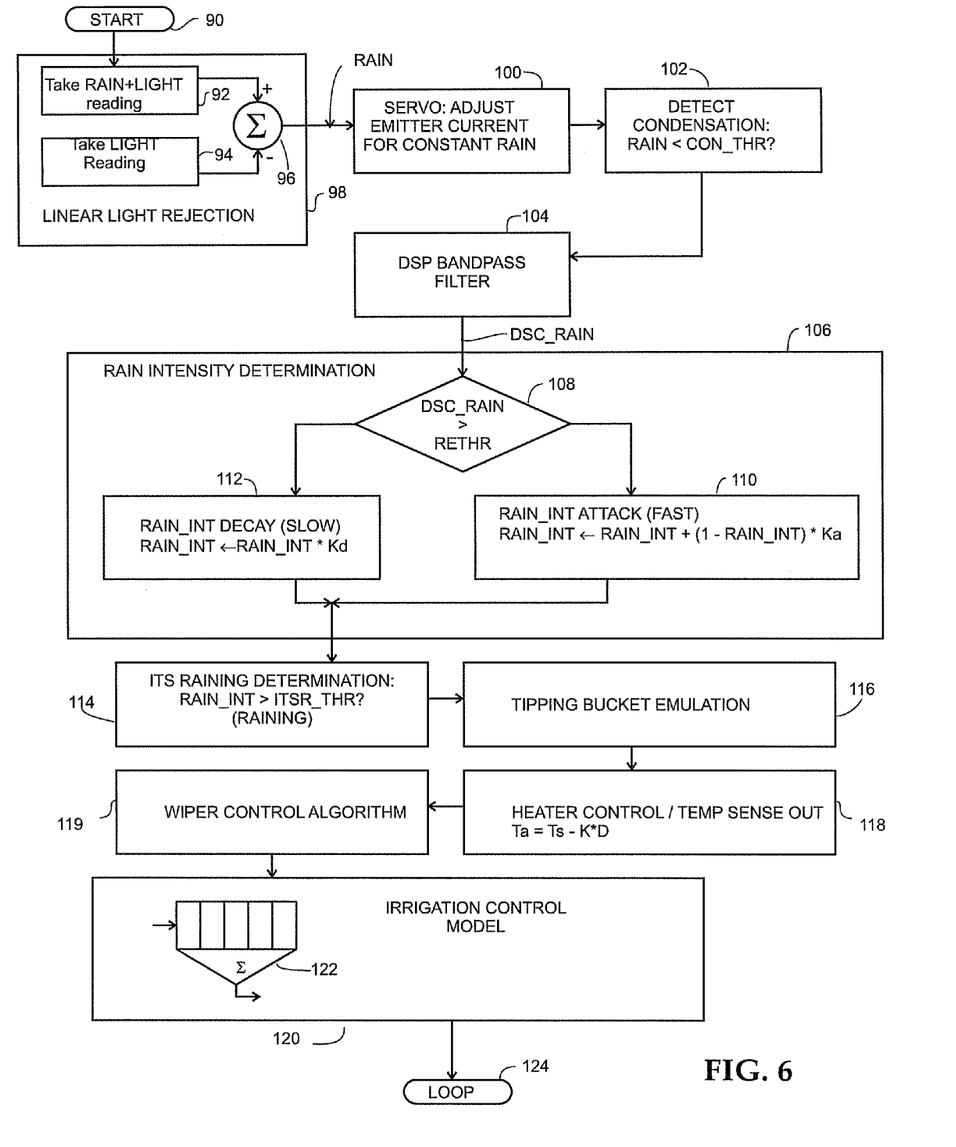
FIG. 6 shows a logic diagram of the primary software components of the moisture sensor according to the present invention.

An overview of the software utilized in the preferred embodiment of moisture sensor 12 is presented in FIG. 6. The software implements an algorithm that, in 1 millisecond intervals commences with the "START" operation 90 of FIG. 6. In operation, the processor takes two readings of the A/D input 74 from transimpedance amplifier 66 in rapid succession. A "RAIN+LIGHT" digital signal or register value is taken when the pulsatile rays 26a, 26b, 26c are present, with the process or step of represented by box 92. A second reading is taken (box 94) when the rays 26a, 26b, 26c are absent, representing a "LIGHT" signal. The "LIGHT" signal is subtracted from "RAIN+LIGHT" in summation step 96, leaving, in effect, only the effect of the intensity of the beams in a signal RAIN. Thus eliminating the majority of ambient light disturbances. The process is referred to as "linear light rejection", shown in the figure as box 98, and as known from U.S. Pat. No. 5,059,877.

The RAIN signal is used to implement an emitter intensity control servo step (box 100) by adjusting the output of pulsatile controlled current source 64. Current source 64 is adjusted so that an average value of RAIN is held to an approximately constant value. Current source 64 is permitted to adjust only a slight amount during each RAIN reading, and thus responds very slowly. Rapid fluctuations of RAIN, such as are caused by impinging rain drops and the like, are not canceled by emitter intensity control servo 100, because the servo responds too slowly to cancel out such pulses. This permits the proper rapid response to each sudden change in RAIN signal due to an impinging raindrop, but properly adjusts the signal strength of light rays 26a, 26b, 26c to compensate for component drift and other factors. This is done by adjusting the output of current source 64. Most importantly, if outer lens surface 16 becomes contaminated, or if the surface 16 degrades due to aging and ultraviolet exposure, the emitter servo will compensate by increasing the output of current source 64 so that the average strength of the beam 26 striking the detector 36 remains constant. The adjustment of the current source is bounded, so that it may never increase beyond a specified level, preferably to no more than 4 times a nominal level. This is sufficient to permit servo 100 to properly compensate for optical path 52 degradation due to surface contamination and other aforementioned factors. The presence of condensation, however, on sensing regions 32a, 32b may occlude the optical path by more than 70%. This is a greater occlusion than can be compensated for by servo 100. To compensate for these conditions, condensation sensing step 102 compares the RAIN value against a compensation threshold (COM THR) Should RAIN fall below this compensation threshold, interface circuit 80 communicates to external equipment that condensation is sensed. It is contemplated that optical path changes due to condensation may also be detected by monitoring servo 100, which attempts to compensate for such changes by, for example, increasing an output current of pulsatile current source 64. A moisture sensor such as the present invention can be useful in HVAC applications, such as humidification. Humidification systems are designed to put as much water into the air as possible, but no so much that water condenses on the ductwork and other HVAC equipment. Water on the duct-work would destroy it. Ideally, the output of the humidification system operates at about 99% relative humidity, but never reaches 100%. Typically, such systems humidify the air to only about 95% relative humidity, to build in some safety factor. The present invention by accurately sensing condensation permits the humidification system to operate with greater efficiency.

As shown in step 104, a DSP band pass filter rejects the dc component of the rain signal, as might be caused by component drift or an interference as well as high frequency fluctuation in RAIN, further decreasing interference, and amplifies the desired, rain-sensing ac component of the RAIN signal. DSP filters such as the one used in the present invention provide gain and extract the desired signal such as the RAIN signal out of the background noise. The result is a discriminated rain (DSC_RAIN) signal or register value that generates a pulse upon each step change in the intensity of received light beams. Thus, each raindrop impinging upon the sensor causes a pulse in DSC_RAIN. Due to the aforementioned steps, the pulses on DSC_RAIN are caused only by the appearance of water on the outside surface, and not because of shadows, component drift, EMI, high relative humidity, insects, or other interfering sources.

With the rain sensing component of RAIN properly discriminated in the form of DSC_RAIN, the software proceeds to process the signal in a manner useful for different chosen applications. The overall intensity of the rainfall is discerned by an intensity extraction algorithm contained within box 106. The algorithm compares DSC_RAIN with a rain event threshold RETHR, with the operation shown as a decision-diamond 108 in FIG. 6, and represented as dotted line RETHR on the graph of FIG. 7. If DSC_RAIN is above threshold RETHR, then an ongoing rain intensity value (RAIN_INT) asymptotically approaches (box 110) a saturation value (255, assuming an 8 bit quantity), or "attacks." If DSC_RAIN is below the threshold RETHR, then RAIN_INT is allowed to asymptotically approach zero, or "decay" (box 112). The attack time (set by constants in software) is much shorter than the decay time. Thus configured, RETHR acts as a threshold for individual raindrop events.

For a long term, statistically averaged rainfall (rain fall is best described statistically as a Laplacian waiting time distribution) RAIN_INT achieves an equilibrium value proportional to the intensity of the rainfall. Thus, RAIN_INT provides a continuous, ongoing estimate of the rate of rainfall impinging upon the outer surface. External equipment may use this estimate (provided by way of interface circuitry 80) for any number of purposes.

For example, modern storm drain systems include control valves to divert runoff water to rivers and lakes, as well as into treatment plants to prevent pollution, depending on rainfall intensity. An accurate measure of rain intensity such as provided by the present invention, can improve such a system. A further example is in the control systems for the seeding of clouds to precipitate rain storms. The RAIN_INT signal provided by the present invention can provide a measurement of the moisture content of a cloud. By contrast, a tipping bucket style rain sensor is wholly inappropriate for deployment on an aircraft.

With the intensity of rainfall established in RAIN_INT, the software may proceed to make a threshold determination of whether or not it is raining. This is done in step 114, producing a binary output RAINING, set high when RAIN_INT exceeds the "its raining" threshold, ITSR THR is a threshold for overall rain intensity, not individual raindrops. This may be communicated to interface 80 to, for example, to close a relay contact. This closure may in turn be used by external equipment to, for example, close a skylight or window. External equipment might retract an awning that would be damaged if left out in the rain.

The software also includes a tipping bucket-emulation operation 116 to convert the RAIN_INT to a series of pulses that emulate a tipping bucket. Emulation operation 116 acts as a digitally controlled oscillator controlled by the value of RAIN_INT. Characteristics of the emulation are determined empirically so that the output corresponds to that which a tipping bucket would have produced in the same location. An alternative method of implementing a tipping bucket is to produce a pulse for each rain event detected in the DSC_RAIN threshold comparison 108. Results of the tipping bucket emulation are communicated via interface 80 as a simple level shift that behaves just as if the present invention were a tipping bucket rain gauge.

For operation at temperatures below freezing, heater control block 118 controls heater 82. By warming sensor housing 18, snow at a temperature of just a few degrees below freezing will still melt on outer lens surface 16 and be detected. This extends the useful range of temperature operation of the rain sensor 12 of the present invention. Extremely cold, dry snow will still generally slide off the sensor without being detected. Heater 82 is under control of processor 62, utilizing temperature sensor 76. The control is that of a conventional thermostat. If the temperature drops below the set point (nominally just above the freezing point of water at 34° F., or 1° C.), then heater 82 turns on. The temperature sensor information is also relayed to external equipment via interface 80. One of the applications for temperature data is as a freeze detector after comparison to a threshold, often utilized by irrigation systems to prevent operation of the system at or below freezing. Other applications may require a reading of outside ambient temperature, Ta. Temperature sensor 76 measures the temperature inside of the rain sensor. As long as heater 82 is off, the temperature inside the rain sensor, Ts will be very close to the outside ambient temperature, Ta. When heater 82 is on, the present invention computes an estimate of the outside ambient temperature by compensating for Ts. More specifically Ta is derived from the measured duty factor D of the heater and measured sensed temperature Ts. The technique is shown as a formula in box 118, and exploits the fact that the thermal resistance between the interior and exterior of rain sensor 12 is predetermined. A prototype of the present invention, for example, exhibits a thermal resistance of 3.9° C. per watt. Additionally, the interface circuitry measures the supply voltage, so that the wattage dissipation of heater 82 can be calculated to adjust the temperature compensation. These factors are used to compute the required constant K used in the compensation.

Functional block 119 uses rain intensity RAIN_INT to provide a wiper control algorithm that produces a WIPER ON output of the interface circuitry 80. This allows the present invention to control wipers designed to enhance the visibility though a sheet of glass or other material. While automotive rain sensors abound, there exist many non-automotive wiper control applications for which automotive rain sensors are inappropriate. For example, large ships have wiper systems on front and side windows, and these windows may be an inch (2.54 cm) thick. This is too thick for automotive rain sensors, which are mounted on the inside surface of the glass. Train locomotive windshields are also too thick for interior glass-mounted automotive rain sensors. It is contemplated that the present invention may be deployed on an exterior portion of such an application, generally in proximity to the window to be wiped. For example, the rain sensor 12 may be deployed near the windshield of a locomotive, and properly control the windshield wipers. This configuration exploits the fact that the rate of rainfall upon the sensor is essentially the same on the sensor and the windshield, even though they may be several feet (a meter or two) apart.

Wiper control block 119 utilizes RAIN_INT to appropriately generate a signal WIPER ON whenever the windshield wiper should be actuating. The external equipment (e.g. ship or locomotive) is arranged to run the wipers whenever WIPER ON signal is logic one or high. When the WIPER ON signal is low, the wipers return to a home or rest position. By way of example, the algorithm may set the WIPER ON signal high whenever RAIN INT exceeds a threshold, say 200 assuming an 8 bit quantity. This causes the controlled wipers to enter a steady slow mode in a steady, medium-intensity rainfall. When RAIN INT drops below a threshold (say, 5) the WIPER ON signal is held low, holding the wipers off. When RAIN_INT falls between these thresholds, the WIPER ON oscillates between high and low, providing for intermittent wipers. The delay time between pulses becomes shorter as RAIN_INT approaches the steady-slow threshold of 200. Similarly, an additional output (not shown) may be provided to cause the external wipers to enter high speed when RAIN_INT exceeds a higher threshold, say 240. Thus arranged, the present invention provides automatic wiper control for applications that are not well served by automotive rain sensors.

In functional block 120, the software calculates an appropriate irrigation control strategy, based on the computed rain intensity, RAIN_INT. A FIFO (First-In, First-Out)/Summing block 122 maintains a weighted average of how much rain has fallen over each of the past several days. Elements of the FIFO can be configured so that the estimate of rainfall may contain data from as long ago as, for example, a month. Longer term rainfall data may be stored in non-volatile memory (EEPROM), so that momentary disruptions in power do not cause the device to forget weeks of data. The immediately preceding 24 hours is weighted more heavily than the day before, and that is in turn weighted more heavily than the day before that, and so on. Thus configured, the software will take into account the rainfall over the past week. So, for example, if there had been an extended downpour three days before, the system is much less likely to call for operation of an irrigation system than if the most recent rainfall event was occurring after an extended dry spell. The commands to suppress operation of the sprinkler system are communicated with interface circuitry 80 in a conventional manner. Additionally, the irrigation control may be configured so that the threshold of irrigation suppression is adjusted in accordance with the longer term prevailing conditions. For example, if the present rain sensor, using the FIFO were to detect that the sensor was subject to a drought lasting for some weeks, it would cause it to be more reluctant to inhibit the irrigation system. Finally, the system loops back (at 124) to start the computations again in 1 mS.

Figures 7, 8:
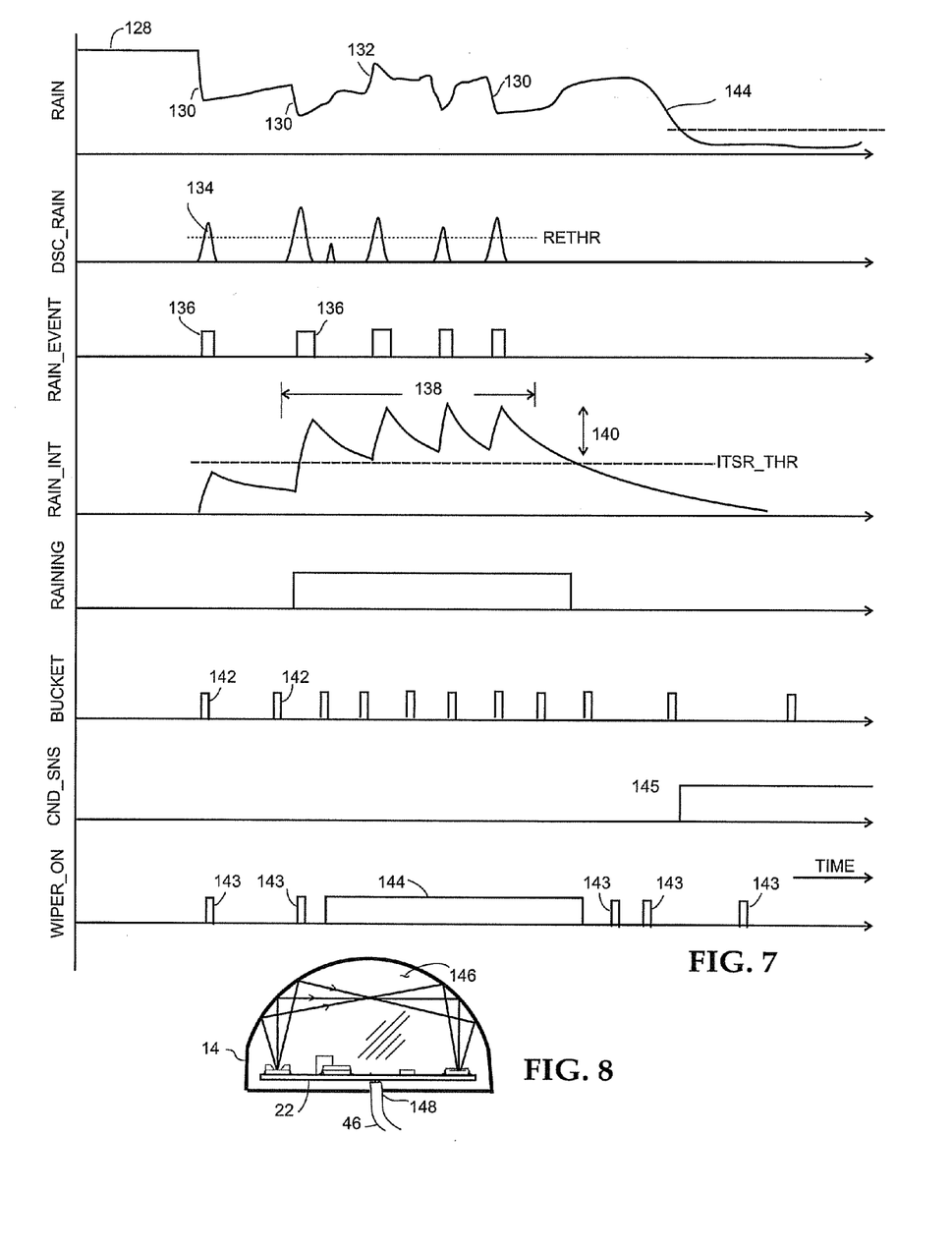
FIG. 7 is a graphical view of a series of signals (or register values) generated in or by various components in the operation of the moisture sensor according to the present invention.
FIG. 8 shows a second embodiment of the rain sensor according to the present invention of illustrating an alternative disposition of the circuit board.

FIG. 7 presents typical signals sent and received within the present moisture sensor 12 in graphical form. The time scale shown is on the order of a second or two between raindrops. The top trace, RAIN, shows the demodulated output of the linear light rejection. A higher value corresponds to a more efficient optical path 52, and a lower value to a path that is partially occluded by the effects of rain drops. Toward the left portion of the graph sensor 12 is dry, and the RAIN assumes a high, dry condition level 128. When a rain drop strikes one of the active emitter or detector areas 32a, 32b, the RAIN signal decreases, as shown at rain event 130. A rain drop falling off one of the emitter or detector active areas 32a, 32b makes the signal increase, such as at 132. In general, the RAIN level will have much low frequency noise as the drops move across the outer surface 16, somewhat at random, moving on and off the emitter or detector active areas 32a, 32b.

The ac components of RAIN are extracted by the DSP discrimination 104, resulting in DSC_RAIN 108. These will result in a series of signal peaks 134 as the value of RAIN changes suddenly. These peaks 134 are compared (step 108)

against a rain-event threshold (shown as dashed line RETHR), and those that exceed the line are converted to a series of binary rain events 136, presented in the trace RAIN_EVENT on FIG. 7. The results of rain intensity extraction algorithm 106 are presented as RAIN_INT as a trace on the graph. The presence of a rain event 136 yields an asymptotic attack 110, corresponding to the block similarly numbered in FIG. 6, and the absence of a rain event corresponds to decay 112. It can be seen that during a period of time 138 when rainfall is approximately constant, and activity on RAIN is of a consistent amount, RAIN will assume a value within a constrained range 140. The value of RAIN_INT is also compared (block 114 of FIG. 6) against a threshold (ITSR_THR), to generate a binary value that corresponds to the fact that "it is raining", shown in FIG. 7 as RAINING. This information is communicated to external equipment via interface circuitry 80.

Additionally, tipping bucket emulation 116 produces a series of pulses 142 that correspond to the pulses that a tipping bucket style rain gauge would have produced, had it been deployed in the same location as moisture sensor 12. On the right side of the graph, the effects of condensation on the RAIN signal are shown at 145, in the form of a relatively slow severe drop in received signal strength. This is compared (step 102) against a threshold CND_SNS. If the signal RAIN drops below this threshold, interface circuitry 80 informs external equipment that condensation is present on the outside surface of the sensor. Further, FIG. 7 shows the output WIPER ON, produced by Wiper Control block 119. A series of wiper pulses 143 indicate intermittent operation of the wiper as RAIN_INT increases, corresponding to increasing intensity of rainfall hitting sensor 12. WIPER ON is held in an on interval for a steady slow interval 140 once RAIN_INT achieves some threshold. A second series of wiper pulses 143 occurs as RAIN_INT decays, with the pulses becoming progressively more widely spaced.

A prototype constructed of the present rain sensor invention has demonstrated, for example, that the optical paths 52 are extremely efficient, usefully transmitting most light rays from the emitter to the detector 36. It may be noted that there is no need for structures to prevent stray light or crosstalk from the emitter to the detector due to optical paths besides those described above; the efficiency of optical path 52 overpowers any crosstalk. A typical raindrop having a diameter of about 6 mm and a volume of about 50 µl results in a decrease in the optical path efficiency of approximately 3%. A decrease of this magnitude is readily discerned by the circuitry and software of the invention. In practice, even very small drops of moisture well under a millimeter in size are easily detected.

It should be appreciated that the present invention can be manufactured at a very low cost. All of the required optical surfaces may be implemented in a single lens 14. Optical CAD analysis reveals that effective focal lengths are long, compared with the geometry of the LEDs, and spherical aberration is low, which has the practical benefit of making the system immune to imperfections of surfaces, and placement, further driving down costs. All electronic components are preferably surface mounted on a single circuit board using conventional, automated techniques, and no parts are especially expensive or exotic. The present invention provides greater sensitivity than even the most precisely manufactured tipping bucket, but is only a fraction of the cost.

FIG. 8 portrays an alternative embodiment of the present invention, wherein circuit board 22 is embedded within lens 14. Such a construction may be realized by filling a mold with a resin 146, fully encapsulating the electronics of the device. The resin may alternatively form the outside surface 16 (as shown in the figure) or be back-filled into a plastic mold (not shown, as it is optically equivalent.) Connecting wires form a watertight seal 148 with resin 146. To maintain the proper optical relationship, Rd is once again between 68% and 80% of Rs. This configuration effectively deletes planar emitter lens 30 and planar detector lens 39. Absent the focal power of each of these lenses, the resulting sensor is thus less efficient than the embodiment of FIG. 1, but still sufficiently efficient for many applications. In this embodiment, the lens 14 itself forms the housing. This embodiment may be preferred for the lowest cost implementations of the present invention.

Lens assembly 14 may be molded of any material suitably clear to the emitter rays 26a, 26b, 26c. Clear acrylic is readily available, or in the case of infrared emitters and detectors, material that is visible to IR but opaque to visible light may be used, for example. Material is considered "clear" if it transmits the wavelength of radiation emitted by the emitters.

Both emitter and detector lens surfaces 30, 39 are preferably planar. Extensive optimization of the present invention utilizing optical CAD software by Zemax, Inc. of Tucson, Ariz., revealed that a plane is the optimal shape. These lens surfaces 30, 39 may alternatively be rendered slightly convex for higher signal strength, or slightly concave for greater area. Also, only the portion of the outer lens surface 16 that folds and focuses the rays needs to be implemented as shown in FIG. 1. Material may be added to the non-active portions of the lens without affecting operation of the invention. Material may be taken away from these regions as well, provided that the cuts into the material do no interfere with the rain sensing rays 26a, 26b, 26c. These additions or deletions of material may be done for aesthetic reasons, or to facilitate a particular flow pattern of water or snow when moving off the sensor 12. Additions or deletions of material may also facilitate mounting for a particular application. While other predetermined geometric shapes are possible, the preferred shape of outer sensing surface 16 is a sphere. The shape may be rendered slightly aspheric by adding polynomial coefficients to the function The invention has been shown assuming moisture, in whatever form, was falling generally down, but the moisture sensor described herein may be deployed at any angle from whence moisture may be conveyed. Descriptions such as "horizontal" or "vertical" used herein should be interpreted to mean with respect to the figures, and not a limitation on how the device may be used. The outer lens surface 16 is preferably smooth, but may be frosted in order to discriminate between frost and liquid water, should an application call for it. A photodiode is preferred for use as light detector 36, because of its inherent electrical linearity, but a phototransistor or CdS photocell may be substituted. The DIP switch as shown represents one way to configure the moisture sensor 12, but it is also contemplated that the device may be configured by using an external pulsatile optical infrared signal properly correlated with the emitter signals and containing digital data. A microprocessor is the preferred method of implementing the required signal processing, but a programmable gate array or other suitable hardware may be used instead. Water is described as the detected source of moisture throughout this document, because detection of water is by far the most common application. Other liquids, such as gasoline, water/chemical solutions, etc., may be detected as well.

In accordance with the provisions of the patent statutes, the invention has been described in what is considered to represent its preferred embodiments. However, it should be noted that the invention can be practiced otherwise than as specifically illustrated and described without departing from its spirit or scope.

What is claimed is:

1. A self-contained optical moisture sensor unit comprising:
   a housing;
   a substantially planar circuit board disposed substantially horizontally in the housing;
   at least one light emitter and at least one light detector mounted on the circuit board;
   a lens having a predetermined geometric shape and being light transmissive, sealingly mounted on the housing, the lens comprising:
      an inner sensing surface and an outer sensing surface, the outer sensing surface being substantially continuously concave in shape relative to the circuit board, and the inner sensing surface also being substantially continuously concave relative to the circuit board, and at a predetermined distance above the at least one light emitter and at least one light detector wherein the moisture sensor has a radial distance Rd which is from 68% to 80% of the radius of the outer sensing surface of the lens Rs; at least one control circuit to control the at least one light emitter and at least one light detector; and
   software to analyze at least the data received by the at least one light detector.

2. The self-contained optical moisture sensor defined in claim 1, wherein at least two light emitters and at least two light detectors are mounted on the circuit board in a predetermined geometric relationship to the lens, and one light emitter and one light detector to the other.

3. The self-contained optical moisture sensor defined in claim 1, wherein the lens has a substantially hemispherical shape.

4. The self-contained optical moisture sensor defined in claim 3, wherein the at least two light emitters and at least two light detectors are operatively coupled to the at least one control circuit.

5. The self-contained optical moisture sensor defined in claim 1, wherein the at least one control circuit comprises a microprocessor which produces a binary output indicating the intensity of rainfall detected by the at least one light detector.

6. The self-contained optical moisture sensor defined in claim 1, wherein the at least one control circuit produces an output to indicate occlusion of the outer sensing surface of the lens due to the presence of condensation thereon.

7. The self-contained optical moisture sensor defined in claim 1, further including a temperature sensor and a heating device.

8. The self-contained optical moisture sensor defined in claim 7, wherein the temperature sensor and at least one control circuit are capable of estimating the ambient temperature in which the moisture sensor is operating.

9. The self-contained optical moisture sensor defined in claim 1, wherein the radial distance Rd is from 70%-75% of the radius of the outer sensing surface of the lens, Rs.

10. The self-contained optical moisture sensor defined in claim 9, wherein the radial distance Rd is about 72% of the radius of the outer sensing surface of the lens, Rs.

11. A self-contained optical moisture sensor unit comprising:
   a housing;
   a substantially planar circuit board disposed substantially horizontally in the housing;
   at least one light emitter and at least one light detector mounted on the circuit board;
   a lens having a predetermined geometric shape and being light transmissive, sealingly mounted on the housing, the lens comprising:
      an inner sensing surface and an outer sensing surface, the outer sensing surface being substantially continuously concave in shape relative to the circuit board, and the inner sensing surface having a center portion being substantially continuously concave relative to the circuit board, and a peripheral planar portion proximate and at a predetermined distance above the at least one light emitter and at least one light detector wherein the moisture sensor has a radial distance Rd which is from 68% to 80% of the radius of the outer sensing surface of the lens Rs; at least one control circuit comprising at least one microprocessor to control the at least one light emitter and at least one light detector; and
   software to analyze at least the data received by the at least one light detector.

12. The self-contained optical moisture sensor defined in claim 11, wherein at least two light emitters and at least two light detectors are mounted on the circuit board in a predetermined geometric relationship to the lens, and one light emitter and one light detector to the other.

13. The self-contained optical moisture sensor defined in claim 11, wherein the lens has a substantially hemispherical shape.

14. The self-contained optical moisture sensor defined in claim 13, wherein the at least two light emitters and at least two light detectors are operatively coupled to the at least one control circuit.

15. The self-contained optical moisture sensor defined in claim 11, wherein the at least one control circuit produces a binary output indicating the intensity of rainfall detected by the at least one light detector.

16. The self-contained optical moisture sensor defined in claim 11, wherein the at least one control circuit produces an output to indicate occlusion of the outer sensing surface of the lens due to the presence of condensation thereon.

17. The self-contained optical moisture sensor defined in claim 11, further including a temperature sensor and a heating device.

18. The self-contained optical moisture sensor defined in claim 17, wherein the temperature sensor and at least one control circuit are capable of estimating the ambient temperature in which the moisture sensor is operating.

19. The self-contained optical moisture sensor defined in claim 11, wherein the radial distance Rd is from 70% to 75% of the radius of the outer sensing surface of the lens, Rs.

20. The self-contained optical moisture sensor defined in claim 11, wherein the at least one control circuit produces an output emulating the output of a tipping-bucket style rain gauge.

* * * * *